US010047191B2

(12) United States Patent
Cheon et al.

(10) Patent No.: US 10,047,191 B2
(45) Date of Patent: Aug. 14, 2018

(54) COMPOUND CONTAINING PHOSPHONIUM ION, EPOXY RESIN COMPOSITION CONTAINING SAME, AND DEVICE MANUFACTURED BY USING SAME

(71) Applicant: SAMSUNG SDI CO., LTD., Yongin-si, Gyeonggi-do (KR)

(72) Inventors: Jin Min Cheon, Uiwang-si (KR); Min Gyum Kim, Uiwang-si (KR); Jung Seob Kim, Uiwang-si (KR); Dong Hwan Lee, Uiwang-si (KR); Hwan Sung Cheon, Uiwang-si (KR); Seung Han, Uiwang-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 268 days.

(21) Appl. No.: 14/907,643

(22) PCT Filed: Feb. 27, 2014

(86) PCT No.: PCT/KR2014/001628
§ 371 (c)(1),
(2) Date: Jan. 26, 2016

(87) PCT Pub. No.: WO2015/012467
PCT Pub. Date: Jan. 29, 2015

(65) Prior Publication Data
US 2016/0159971 A1    Jun. 9, 2016

(30) Foreign Application Priority Data

Jul. 23, 2013 (KR) .................. 10-2013-0087028
Jan. 16, 2014 (KR) .................. 10-2014-0005608

(51) Int. Cl.
*C08G 59/68* (2006.01)
*C08L 63/00* (2006.01)
*C07F 9/54* (2006.01)
*C07D 239/42* (2006.01)
*C07C 311/51* (2006.01)
*C08G 59/62* (2006.01)
*C08G 59/24* (2006.01)
*C08L 63/04* (2006.01)

(52) U.S. Cl.
CPC .......... *C08G 59/688* (2013.01); *C07C 311/51* (2013.01); *C07D 239/42* (2013.01); *C07F 9/5442* (2013.01); *C07F 9/5456* (2013.01); *C08G 59/245* (2013.01); *C08G 59/621* (2013.01); *C08L 63/00* (2013.01); *C08L 63/04* (2013.01); *C08L 2205/05* (2013.01)

(58) Field of Classification Search
None
See application file for complete search history.

(56) References Cited

U.S. PATENT DOCUMENTS

| 2005/0033005 A1* | 2/2005 | Kocher | C07D 241/20 528/44 |
| 2005/0033006 A1* | 2/2005 | Kocher | B01J 31/0222 528/44 |

FOREIGN PATENT DOCUMENTS

| CN | 1600809 A | 3/2005 | |
| CN | 1833003 A | 9/2006 | |
| CN | 101273076 A | 9/2008 | |
| EP | 0485008 A1 * | 5/1992 | ............ C08G 18/10 |
| JP | 2005048047 A | 2/2005 | |
| JP | 4784698 B1 | 10/2011 | |
| JP | 2011-219740 A | 11/2011 | |
| JP | 2011-231243 A | 11/2011 | |
| JP | 2013-087137 A * | 5/2013 | ............ C08G 59/62 |
| WO | WO 2014-024663 A1 | 2/2014 | |

OTHER PUBLICATIONS

Machine translation of JP 2013-087137 A (no date).*
Office Action dated Dec. 2, 2016 in the corresponding Chinese Patent Application No. 201480041323.3.

* cited by examiner

*Primary Examiner* — Michael J Feely
(74) *Attorney, Agent, or Firm* — Lee & Morse, P.C.

(57) ABSTRACT

The present invention relates to a compound containing phosphonium ion of a chemical formula 1, an epoxy resin composition containing the same, and a device manufactured by using the same.

19 Claims, No Drawings

COMPOUND CONTAINING PHOSPHONIUM ION, EPOXY RESIN COMPOSITION CONTAINING SAME, AND DEVICE MANUFACTURED BY USING SAME

CROSS REFERENCE TO RELATED APPLICATIONS

This is the U.S. national phase application based on PCT Application No. PCT/KR2014/001628, filed Feb. 27, 2014, which is based on Korean Patent Application Nos. 10-2013-0087028, filed Jul. 23, 2013, and 10-2014-0005608, filed Jan. 16, 2014, the entire contents of all of which are hereby incorporated by reference.

TECHNICAL FIELD

The present invention relates to a phosphonium ion-containing containing compound, an epoxy resin composition including the same, and an apparatus manufactured using the same.

BACKGROUND ART

Epoxy resins have low reaction shrinkage, excellent electrical, mechanical properties, and high processability and chemical resistance, and are used as a matrix and coating for electric, electronic, construction, and composite materials. For example, epoxy resins are used for encapsulation of semiconductor devices, adhesive films, insulating resin sheets such as prepregs, circuit boards, solder resists, underfills, die bonding agents, and component replenishing resins.

Generally, such an epoxy resin is used after being mixed with a curing agent to be a thermosetting material rather than being used alone. Here, since properties of the epoxy resin depend on a three-dimensional structure created after curing, selection of the curing agent is important. Although many curing agents for epoxy resins have been developed, a curing catalyst is used together in order to catalyze curing reaction. In an apparatus using an epoxy resin composition, there is a need for a curing agent having low temperature curability that allows the rein composition to be cured at low temperature for enhancement of productivity and high storage stability that catalyzes curing only at a desired temperature while not exhibiting catalytic activity at other temperatures for improvement of handling performance during distribution and storage. Since an adduct of triphenylphosphine and 1,4-benzoquinone, as a curing catalyst, catalyzes curing even at relatively low temperatures, there are problems in that, when an epoxy resin composition is mixed with other components before curing, the epoxy resin composition is partially cured by heat generated from the mixture system or externally applied heat, and in that after completion of mixing, the epoxy resin composition can undergo curing even during storage at room temperature and thus has poor storage stability. Such curing can cause the epoxy resin composition to exhibit increase in viscosity and deterioration in fluidity when the epoxy resin composition is liquid, and can cause the epoxy resin composition to exhibit viscosity when the epoxy resin composition is solid, and such a state change is not uniform within the epoxy resin composition. As a result, when the epoxy resin composition is actually cured at high temperature, the epoxy resin composition can suffer from deterioration in moldability due to deterioration in fluidity, and can cause deterioration in mechanical, electrical and chemical properties of a molded article.

DISCLOSURE

Technical Problem

It is an aspect of the present invention to provide a curing catalyst for epoxy resin compositions, which can catalyze curing of an epoxy resin.

It is another aspect of the present invention to provide a curing catalyst for epoxy resin compositions, which can catalyze curing of an epoxy resin even at low temperature.

It is a further aspect of the present invention to provide a curing catalyst for epoxy resin compositions, which exhibits high storage stability to catalyze curing only at a desired curing temperature while not exhibiting any catalytic activity at other temperatures.

Technical Solution

In accordance with one aspect of the present invention, a phosphonium ion-containing compound may be represented by Formula 1:

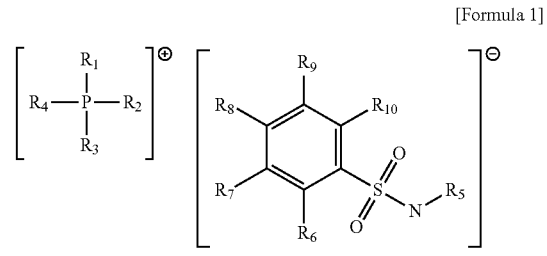

[Formula 1]

(where $R_1$, $R_2$, $R_3$, $R_4$, $R_5$, $R_6$, $R_7$, $R_8$, $R_9$, $R_{10}$ are the same as defined in the following detailed description).

In accordance with another aspect of the present invention, an epoxy resin composition may include an epoxy resin, a curing agent, and a curing catalyst, wherein the curing catalyst may include the phosphonium ion-containing compound as set forth above.

In accordance with a further aspect of the present invention, an apparatus may be manufactured using the epoxy resin composition as set forth above.

Advantageous Effects

The present invention provides a compound for promoting curing, which can catalyze curing of an epoxy resin and catalyze curing of an epoxy resin even at low temperatures. In addition, the present invention provides a curing catalyst for epoxy resin compositions, which exhibits high storage stability to catalyze curing only at a desired curing temperature while not exhibiting any catalytic activity at other temperatures. Further, the present invention provides a compound for promoting curing, which can minimize change in viscosity of a mixture including an epoxy resin, a curing agent, and the like within predetermined ranges of time and temperature, thereby ensuring that an epoxy resin composition obtained after curing at high temperature does not exhibit any deterioration in moldability due to decrease in flowability, and a molded product manufactured using the epoxy resin composition does not suffer from deterioration in mechanical, electrical, and chemical properties.

BEST MODE

One aspect of the present invention relates to a phosphonium ion-containing compound. The phosphonium ion-containing compound includes a phosphonium cation and a sulfonamide anion, and may be represented by, for example, Formula 1:

[Formula 1]

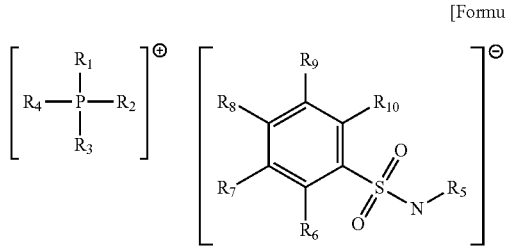

(where $R_1$, $R_2$, $R_3$, and $R_4$ are each independently hydrogen, a substituted or unsubstituted $C_1$ to $C_{10}$ alkyl group, a substituted or unsubstituted $C_3$ to $C_{10}$ cycloalkyl group, a substituted or unsubstituted $C_6$ to $C_{20}$ aryl group, or a substituted or unsubstituted $C_7$ to $C_{21}$ arylalkyl group;

$R_5$ is hydrogen, a substituted or unsubstituted $C_1$ to $C_{10}$ alkyl group, a substituted or unsubstituted $C_6$ to $C_{20}$ aryl group, a substituted or unsubstituted $C_3$ to $C_{20}$ cycloalkyl group, a substituted or unsubstituted $C_2$ to $C_{20}$ heterocycloalkyl group, a substituted or unsubstituted $C_7$ to $C_{20}$ arylalkyl group, a substituted or unsubstituted $C_3$ to $C_{20}$ heteroaryl group, or a compound represented by Formula 2:

[Formula 2]

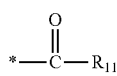

(where * is a binding site to N in Formula 1, and $R_1$ is a substituted or unsubstituted $C_1$ to $C_{10}$ alkyl group, a substituted or unsubstituted $C_6$ to $C_{20}$ aryl group, a substituted or unsubstituted $C_3$ to $C_{10}$ cycloalkyl group, or a substituted or unsubstituted $C_7$ to $C_{20}$ arylalkyl group); and $R_6$, $R_7$, $R_8$, $R_9$, and $R_{10}$ are each independently hydrogen, a substituted or unsubstituted $C_1$ to $C_{10}$ alkyl group, a substituted or unsubstituted $C_6$ to $C_{20}$ aryl group, a substituted or unsubstituted $C_7$ to $C_{21}$ arylalkyl group, or —NR'R" (where R' and R" are each independently hydrogen, a $C_1$ to $C_{10}$ alkyl group, a $C_6$ to $C_{20}$ aryl group, or a $C_7$ to $C_{21}$ arylalkyl group)).

As used herein, the term "substituted" in "substituted or unsubstituted" means that at least one hydrogen atom in the corresponding functional groups is substituted with a hydroxyl group, an amino group, a nitro group, a halogen atom, a unsubstituted $C_1$ to $C_{10}$ alkyl group, a $C_6$ to $C_{20}$ aryl group, a $C_3$ to $C_{10}$ cycloalkyl group, a $C_7$ to $C_{21}$ arylalkyl group, or a $C_1$ to $C_{10}$ heteroalkyl group. As used herein, the term "aryl group" refers to a substituent, in which all elements in the cyclic substituent have p-orbitals and the p-orbitals form a conjugated system, and the aryl group include mono- or fused functional groups (namely, rings of carbon atoms sharing adjacent electron pairs). As used herein, the term "heteroaryl group" means an aryl group in which one to three atoms selected from the group consisting of nitrogen, oxygen, sulfur and phosphorus are included and the other atoms are carbon. As used herein, the term "hetero" in "heterocycloalkyl group", "heteroaryl group", "heterocycloalkylene group", and "heteroarylene group" refers to an atom which is nitrogen, oxygen, sulfur or phosphorus.

For example, $R_1$, $R_2$, $R_3$, and $R_4$ are each independently a substituted or unsubstituted $C_6$ to $C_{10}$ aryl group or a substituted or unsubstituted $C_7$ to $C_{12}$ arylalkyl group; $R_5$ is a substituted or unsubstituted $C_1$ to $C_5$ alkyl group, a substituted or unsubstituted $C_3$ to $C_{20}$ heteroaryl group, or a compound represented by Formula 2; $R_8$ is —NH$_2$, —NHR', or a substituted or unsubstituted $C_1$ to $C_5$ alkyl group; $R_6$, $R_7$, $R_9$, and $R_{10}$ are each independently hydrogen, a $C_1$ to $C_{10}$ alkyl group, or a $C_6$ to $C_{10}$ aryl group.

For example, $R_5$ is a substituted or unsubstituted $C_1$ to $C_4$ alkyl group, a substituted or unsubstituted $C_3$ to $C_{20}$ heteroaryl group, for example, a diazinyl group such as a pyrazinyl group, a pyrimidinyl group, and a pyridazinyl group: a pyridyl group; a triazinyl group; a thiazol group; an oxazine group; an isoxazol group; a furanyl group; a thiophenyl group; a quinolinyl group; an indolyl group; a purine group; a benzofuran group; a benzopyridine group; a benzothiophene group; a benzothiepine group; a benzoquinoline group; a pyrazole group; a pyran group; an azepine group; a pyrimidinone group; a thiadiazine group; a quinoxaline group; a pyrroline group; a tetrahydropyridine group; an oxazoline group; a dihydrothiadiazine group; or a compound represented by Formula 2 in which $R_{11}$ is a substituted or unsubstituted $C_1$ to $C_5$ alkyl group or a substituted or unsubstituted $C_6$ to $C_{10}$ aryl group, for example, an acetyl group or a benzoyl group.

The phosphonium ion-containing compound may have a glass transition temperature of about 100° C. to about 130° C., for example, about 120° C. to about 125° C., and may have a curing initiation temperature of about 90° C. to about 120° C. and a curing peak temperature of about 120° C. to about 180° C., as measured by differential scanning calorimetry (DSC). Within this range, the phosphonium ion-containing compound can provide low temperature curability. As used herein, the curing initiation temperature means a temperature at which exothermic polymerization starts upon heating an epoxy resin including the phosphonium ion-containing compound at a constant heating rate, and the curing peak temperature means a temperature at which exothermic peak is highest in reaction under the above conditions.

The phosphonium ion-containing compound may be a water-insoluble compound or a water-soluble compound in the form of a salt.

The phosphonium ion-containing compound may be used as a latent curing catalyst for a composition including at least one of epoxy resins and curing agent. In other words, the phosphonium ion-containing compound decomposes into a phosphine compound and a cationic/anionic compound at about 90° C. to about 175° C., as in Reaction Formula 1, upon application of external energy such as heat.

[Reaction Formula 1]

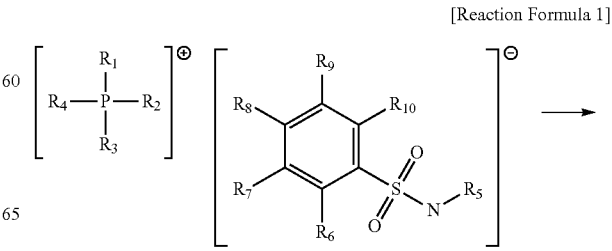

-continued

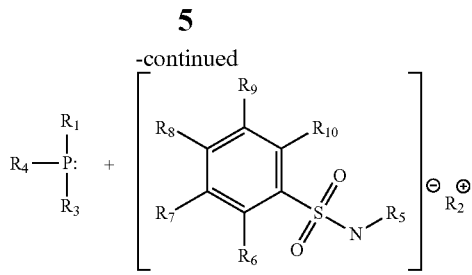

(where $R_1$, $R_2$, $R_3$, $R_4$, $R_5$, $R_6$, $R_7$, $R_8$, $R_9$, and $R_{10}$ are the same as defined in Formula 1).

Curing reaction may be catalyzed by reaction of the phosphine compound with an epoxide group in an epoxy resin to perform ring opening, followed by reacting with a hydroxyl group in the epoxy resin to perform ring opening of the epoxide group, and then by reaction of a terminal chain of the activated epoxy resin with an epoxide.

The phosphonium ion-containing compound can provide an epoxy resin composition capable of catalyzing curing of an epoxy resin and a curing agent and capable of securing low temperature curability and high storage stability while minimizing viscosity change in a mixture including the compound together with an epoxy resin, a curing agent and the like even within desired ranges of time and temperature. As used herein, the term "storage stability" refers to the ability to catalyze curing only at a desired curing temperature while not exhibiting any catalytic activity at other temperatures. As a result, it is possible to store the epoxy resin composition for a long time without causing viscosity change. Generally, curing reaction can cause increase in viscosity and deterioration in flowability when the epoxy resin composition is liquid, and can exhibit viscosity when the epoxy resin composition is solid.

In one embodiment, the epoxy resin may have two or more epoxy groups per molecule. Examples of the epoxy resin may include bisphenol type epoxy resins such as bisphenol A type epoxy resins or bisphenol F type epoxy resins, phenol novolac type epoxy resins, tert-butyl catechol type epoxy resins, naphthalene type epoxy resins, glycidyl amine type epoxy resins, phenol aralkyl type epoxy resins, cresol novolac type epoxy resins, biphenyl type epoxy resins, linear aliphatic epoxy resins, alicyclic epoxy resins, heterocyclic epoxy resins, spiro ring-containing epoxy resins, cyclohexane dimethanol type epoxy resins, and halogenated epoxy resins, without being limited thereto. These epoxy resins may be used alone or in combination thereof. For example, the epoxy resin may have two or more epoxy groups and one or more hydroxyl groups per molecule. The epoxy resin may include at least one of a solid phase epoxy resin and a liquid phase epoxy resin, and a solid phase epoxy resin is preferably used.

In one embodiment, the curing agent may include phenolaralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins prepared from bisphenol A and resol, polyhydric phenol compounds including tris(hydroxyphenyl)methane and dihydroxybiphenyl, acid anhydrides including maleic anhydride and phthalic anhydride, and aromatic amines including meta-phenylenediamine, diaminodiphenylmethane, diaminodiphenylsulfone, and the like. Preferably, the curing agent is a phenol resin having one or more hydroxyl groups.

The phosphonium ion-containing compound may be present in an amount of about 0.01 wt % to about 10 wt %, for example, about 0.01 wt % to about 5 wt %, for example, about 0.02 wt % to about 1.5 wt %, for example, about 0.05 wt % to about 1.5 wt %. Within this range, the epoxy resin composition can secure flowability without delaying time for curing reaction.

The phosphonium ion-containing compound may be prepared by a typical method. For example, the phosphonium ion-containing compound may be prepared by reacting a phosphonium cation-containing compound represented by Formula 3 with an anion-containing compound represented by Formula 4:

[Formula 3]

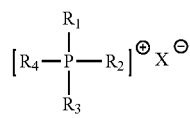

(where $R_1$, $R_2$, $R_3$, and $R_4$ are the same as defined in Formula 1, and X is halogen)

[Formula 4]

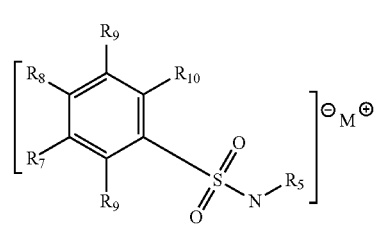

(where $R_5$, $R_6$, $R_7$, $R_8$, $R_9$, and $R_{10}$ are the same as defined in Formula 1, and M is an alkali metal or Ag).

Halogen is fluorine, chlorine, bromine, or iodine, and the alkali metal is lithium, sodium, rubidium, cesium, or francium.

The phosphonium cation-containing compound may be prepared by reacting a phosphine compound with an alkyl halide, an aryl halide, an aralkyl halide, or the like in the presence of a solvent or may be a phosphonium cation-containing salt. Examples of the phosphine compound may include triphenylphosphine, methyldiphenylphosphine, dimethylphenylphosphine, ethyldiphenylphosphine, diphenylpropylphosphine, isopropyldiphenylphosphine, and diethylphenylphosphine, without being limited thereto. The anion-containing compound may be an anion-containing salt.

Reaction between the phosphonium cation-containing compound represented by Formula 3 and the anion-containing compound represented by Formula 4 can be performed in an organic solvent such as methylene chloride, acetonitrile, N,N-dimethylformamide, and toluene at a temperature of about 10° C. to about 50° C., for example, about 20° C. to about 30° C., for about 1 to 30 hours, for example, for about 10 to 30 hours. The phosphonium cation-containing compound and the anion-containing compound may be reacted in a mole ratio of about 1:0.9 to about 1:2. Reaction may be performed by mixing the phosphonium cation-containing compound represented by Formula 3 and the anion-containing compound represented by Formula 4, or may be performed by reacting a phosphine compound with an alkyl halide, an aryl halide, an aralkyl halide, or the like to prepare the phosphonium cation-containing compound, followed by adding the anion-containing compound thereto in-situ without an additional separation process.

Another aspect of the present invention relates to an epoxy resin composition. The epoxy resin composition may include an epoxy resin, a curing agent, and a curing catalyst, wherein the curing catalyst may include the phosphonium ion-containing compound as set forth above. As a result, the epoxy resin composition can be cured at low temperature and can exhibit excellent storage stability.

Epoxy Resin

The epoxy resin may include bisphenol type epoxy resins, such as bisphenol A type epoxy resins or bisphenol F type epoxy resins, phenol novolac type epoxy resins, tert-butyl catechol type epoxy resins, naphthalene type epoxy resins, glycidyl amine type epoxy resins, phenol aralkyl type epoxy resins, cresol novolac type epoxy resins, biphenyl type epoxy resins, linear aliphatic epoxy resins, alicyclic epoxy resins, heterocyclic epoxy resins, spiro ring-containing epoxy resins, cyclohexane dimethanol type epoxy resins, and halogenated epoxy resins. These epoxy resins may be used alone or in combination thereof.

In one embodiment, the epoxy resin may be a biphenyl type epoxy resin represented by Formula 5 or a phenol aralkyl type epoxy resin represented by Formula 6:

about 2 wt % to about 17 wt %, for example, about 3 wt % to about 15 wt %, for example, about 3 wt % to about 12 wt %, in the composition. Within this range, the composition can secure curability.

Curing Agent

The curing agent may include phenol aralkyl type phenol resins, phenol novolac type phenol resins, xyloc type phenol resins, cresol novolac type phenol resins, naphthol type phenol resins, terpene type phenol resins, multifunctional phenol resins, dicyclopentadiene-based phenol resins, novolac type phenol resins prepared from bisphenol A and resol, polyhydric phenol compounds including tris(hydroxyphenyl)methane and dihydroxybiphenyl, acid anhydrides including maleic anhydride and phthalic anhydride, and aromatic amines including meta-phenylenediamine, diaminodiphenylmethane, diaminodiphenylsulfone, and the like. The curing agent may be a phenol resin having one or more hydroxyl groups.

In one embodiment, the curing agent may be a xyloc type phenol resin represented by Formula 7 or a phenol aralkyl type phenol resin represented by Formula 8:

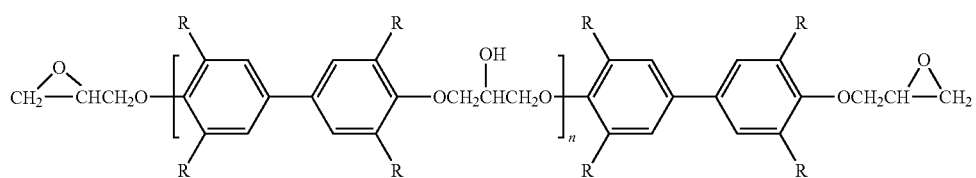

[Formula 5]

(where R is a $C_1$ to $C_4$ alkyl group, and n ranges from 0 to 7 on average.)

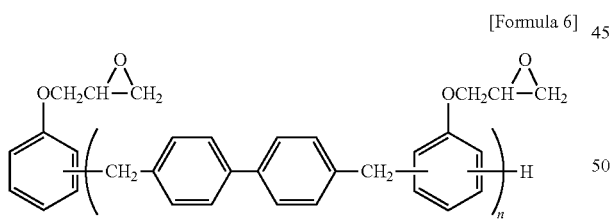

[Formula 6]

(where n ranges from 1 to 7 on average).

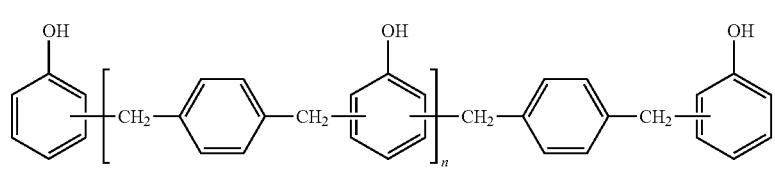

[Formula 7]

The epoxy resin may be present, in terms of solid content, in an amount of about 1 wt % to about 90 wt %, for example, (where n ranges from 0 to 7 on average.)

[Formula 8]

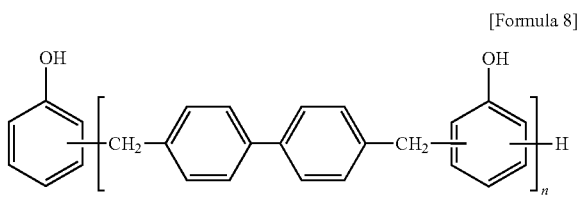

(where n ranges from 1 to 7 on average)

The curing agent may be present, in terms of solid content, in an amount of about 0.1 wt % to about 90 wt %, for example, about 0.5 wt % to about 13 wt %, for example, about 1 wt % to about 10 wt %, for example, about 2 wt % to 8 wt % in the composition. Within this range, the composition can secure curability.

The curing catalyst may include the phosphonium ion-containing compound according to one embodiment of the present invention.

The epoxy resin composition may further include a non-phosphonium curing catalyst which does not contain phosphonium. The non-phosphonium curing catalyst may include tertiary amines, organometallic compounds, organophosphorus compounds, imidazole, boron compounds, and the like. Examples of tertiary amines may include benzyldimethylamine, triethanolamine, triethylenediamine, diethylaminoethanol, tri(dimethylaminomethyl)phenol, 2,2-(dimethylaminomethyl)phenol, 2,4,6-tris(diaminomethyl) phenol, tri-2-ethyl hexanoate, and the like. Examples of organometallic compounds include chromium acetylacetonate, zinc acetylacetonate, nickel acetylacetonate, and the like. Examples of organophosphorus compounds may include tris-4-methoxyphosphine, triphenylphosphine, triphenylphosphine triphenylborane, triphenylphosphine-1,4-benzoquinone adducts, and the like. Examples of imidazole may include 2-methylimidazole, 2-phenylimidazole, 2-aminoimidazole, 2-methyl-1-vinylimidazole, 2-ethyl-4-methylimidazole, 2-heptadecyl imidazole, and the like. Examples of boron compounds may include triphenylphosphine tetraphenyl borate, tetraphenyl borate, trifluoroborane-n-hexylamine, trifluoroborane monoethylamine, tetrafluoroborane triethylamine, tetrafluoroboraneamine, and the like. In addition, it is possible to use 1,5-diazabicyclo[4.3.0]non-5-ene (DBN), 1,8-diazabicyclo[5.4.0]undec-7-ene (DBU), phenol novolac resin salts, and the like. In addition, the curing catalyst may be used in the form of adducts obtained by pre-reacting the curing catalyst with an epoxy resin or a curing agent.

The phosphonium ion-containing compound according to one embodiment may be present in an amount of about 10 wt % to about 100 wt %, for example, about 60 wt % to about 100 wt %, based on the total weight of the curing catalyst. Within this range, the epoxy resin composition can secure flowability without delaying time for curing reaction.

The curing catalyst may be present in an amount of about 0.01 wt % to about 10 wt %, for example, about 0.01 wt % to about 5 wt %, for example, about 0.02 wt % to about 1.5 wt %, for example, 0.05 wt % to 2.0 wt %, in the epoxy resin composition. Within this range, the epoxy resin composition can secure flowability without delaying time for curing reaction.

The epoxy resin composition may further include a typical additive. In one embodiment, the additive may include at least one of a coupling agent, a release agent, a stress reliever, a crosslinking enhancer, a leveling agent, and a coloring agent.

The coupling agent may include at least one of epoxysilane, aminosilane, mercaptosilane, alkylsilane, and alkoxysilane, without being limited thereto. The coupling agent may be present in an amount of about 0.1 wt % to about 1 wt % in the epoxy resin composition.

The release agent may include at least one of paraffin wax, ester wax, higher fatty acids, metal salts of higher fatty acids, natural fatty acids, and natural fatty acid metal salts. The release agent may be present in an amount of about 0.1 wt % to about 1 wt % in the epoxy resin composition.

The stress reliever may include at least one of modified silicone oil, silicone elastomers, silicone powder, and silicone resin, without being limited thereto. The stress reliever may be optionally present in an amount of about 6.5 wt % or less, for example, about 1 wt % or less, for example, about 0.1 wt % to about 1 wt % in the epoxy resin composition. As the modified silicone oil, any silicone polymers having good heat resistance may be used. The modified silicone oil may include about 0.05 wt % to about 1.5 wt % of a silicone oil mixture based on the total weight of the epoxy resin composition, wherein the mixture includes at least one of silicone oil having an epoxy functional group, silicone oil having an amine functional group, silicone oil having a carboxyl functional group, and a combination thereof. However, if the amount of the silicone oil is greater than about 1.5 wt %, surface contamination occurs easily and lengthy resin bleed can be encountered. If the amount of the silicone oil is less than 0.05 wt %, there can be a problem in that sufficiently low modulus of elasticity cannot be obtained. In addition, the silicone powder having an average particle diameter of about 15 m or less is particularly preferred in that the powder does not deteriorate moldability. The silicone powder may be optionally present in an amount of about 5 wt % or less, for example, about 0.1 wt % to about 5 wt %, based on the total weight of the epoxy resin composition.

The coloring agent may be carbon black or the like and be present in an amount of about 0.1 wt % to about 3 wt % in the epoxy resin composition.

The additive may be present in an amount of about 0.1 wt % to about 10 wt %, for example, about 0.1 wt % to about 3 wt %, in the epoxy resin composition.

The epoxy resin composition may further include inorganic fillers. The inorganic fillers are used to improve mechanical properties of the epoxy resin composition while reducing stress in the epoxy resin composition. Examples of the inorganic fillers include at least one of fused silica, crystalline silica, calcium carbonate, magnesium carbonate, alumina, magnesia, clay, talc, calcium silicate, titanium oxide, antimony oxide, and glass fibers.

Fused silica having a low coefficient of linear expansion is preferred in terms of stress reduction. The fused silica refers to amorphous silica having a specific gravity of 2.3 or less. The fused silica may be prepared by melting crystalline silica or may include amorphous silica products synthesized from various raw materials. Although the shape and particle diameter of the fused silica are not particularly limited, the inorganic fillers may include about 40 wt % to about 100 wt % of a fused silica mixture based on the total weight of the inorganic fillers, wherein the fused silica mixture includes about 50 wt % to about 99 wt % of spherical fused silica having an average particle diameter of about 5 m to about 30 m and about 1 wt % to about 50 wt % of spherical fused silica having an average particle diameter of about 0.001 m to about 1 m. The inorganic fillers may also be adjusted to a maximum particle diameter of about 45 m, about 55 m or about 75 m, depending upon application of the epoxy resin composition. Although the spherical fused silica may include conductive carbon as a foreign substance on the surface of silica, it is essential for the spherical fused silica to incorporate a smaller amount of polar foreign substances.

The inorganic fillers may be present in an appropriate amount depending upon desired physical properties of the epoxy resin composition, for example, moldability, low-stress properties, and high-temperature strength. Specifically, the inorganic fillers may be present in an amount of about 70 wt % to about 95 wt %, for example, about 75% to about 92 wt %, based on the total weight of the epoxy resin composition. Within this range, the epoxy resin composition can secure good flame resistance, flowability, and reliability.

The epoxy resin composition is curable at low temperature. For example, a curing initiation temperature may range from about 90° C. to about 120° C. Within this range, the epoxy resin composition can be cured at low temperature, thereby securing curing at low temperature.

The epoxy resin composition exhibits high storage stability by including the phosphonium ion-containing compound. Thus, the epoxy resin composition does not undergo curing when stored in a predetermined temperature range for a predetermined period of time, whereby viscosity of the epoxy resin composition shows only slight change. In one embodiment, the epoxy resin composition may have a rate of viscosity change of about 16% or less, for example, about 15.5% or less, as calculated according to Equation 1:

$$\text{Rate of viscosity change} = |B-A|/A \times 100 \quad \text{[Equation 1]}$$

(where A is the viscosity (unit: cPs) of the epoxy resin composition as measured at 25° C., and B is the viscosity (unit: cPs) of the epoxy resin composition as measured at 25° C. after leaving the epoxy resin composition at 25° C. for 24 hours). Within this range, since the epoxy resin composition exhibits high storage stability, curing of the epoxy resin composition is catalyzed only at a desired curing temperature, and catalytic activity is not exhibited at other curing temperatures. In addition, the epoxy resin composition does not suffer deterioration in moldability due to poor flowability when undergoing curing reaction at high temperature, thereby preventing degradation in mechanical, electrical, and chemical properties of a molded product manufactured using the resin composition.

The epoxy resin composition may have a flow length of about 59 to 75 inches as measured using a transfer molding press at 175° C. under a load of 70 kgf/cm$^2$ in accordance with EMMI-1-66. Within this range, the epoxy resin composition can be used for desired applications.

The epoxy resin composition may have a curing shrinkage of less than about 0.4%, for example, about 0.01% to about 0.39%, as calculated according to Equation 2:

$$\text{Curing shrinkage} = |C-D|/C \times 100 \quad \text{[Equation 2]}$$

(where C is the length of a specimen obtained by transfer molding of the epoxy resin composition at 175° C. under a load of 70 kgf/cm$^2$, and D is the length of the specimen after post-curing the specimen at 170° C. to 180° C. for 4 hours and cooling). Within this range, curing shrinkage is low and the epoxy resin composition can be used for desired applications.

The epoxy resin composition according to the present invention can be used in a broad range of applications requiring such an epoxy resin composition in encapsulation of semiconductor devices, adhesive films, insulating resin sheets such as prepregs and the like, circuit substrates, solder resists, underfills, die bonding materials, and component replenishing resins, without being limited thereto.

(1) Encapsulation of Semiconductor Device

The epoxy resin composition according to the present invention may be used to encapsulate a semiconductor device, and include an epoxy resin, a curing agent, a phosphonium compound-containing curing catalyst, inorganic fillers, and additives.

In one embodiment, the epoxy resin may be present in an amount of about 2 wt % to about 17 wt %, for example, about 3 wt % to about 12 wt % in the composition. Within this range, the epoxy resin composition can exhibit excellent flowability, flame retardancy, and reliability. The phosphonium ion compound-containing curing catalyst may be present in an amount of about 0.01 wt % to about 5 wt %, for example, about 0.05 wt % to about 1.5 wt % in the composition. Within this range, since the amount of unreacted epoxy groups and phenolic hydroxyl groups can be reduced, the epoxy resin composition can exhibit excellent reliability. The curing agent may be present in an amount of about 0.5 wt % to about 13 wt %, for example, about 2 wt % to about 8 wt % in the composition. Within this range, since the amount of unreacted epoxy groups and phenolic hydroxyl groups can be reduced, the epoxy resin composition can exhibit excellent reliability. The inorganic fillers may be present in an amount of about 70 wt % to about 95 wt %, for example, about 75 wt % to about 92 wt % in the composition. Within this range, the epoxy resin composition can exhibit excellent flowability, flame retardancy, and reliability. The additives may be present in an amount of about 0.1 wt % to about 10 wt %, for example, about 0.1 wt % to about 3 wt %.

The epoxy resin in the epoxy resin composition may be used alone or in the form of adducts, such as a melt master batch, obtained by pre-reaction of the epoxy resin with additives such as a curing agent, a curing catalyst, a release agent, a coupling agent, and a stress reliever. Although the method of preparing the epoxy resin composition is not particularly limited, the epoxy resin composition may be prepared by a process in which components of the composition are mixed uniformly and sufficiently using a Henschel mixer or a Lödige mixer, followed by melt kneading using a roll mill or a kneader at about 90° C. to about 120° C., and then cooling and pulverizing.

As a method for encapsulating a semiconductor device using the epoxy resin composition obtained according to the present invention, low-pressure transfer molding may be generally used. However, it should be understood that injection molding or casting may also be employed for molding of the epoxy resin composition. The semiconductor device that can be fabricated by such a molding process may include a copper lead frame, an iron lead frame, an iron lead frame pre-plated with at least one metal selected from among nickel, copper and palladium, or an organic laminate frame.

(2) Adhesive Film

The epoxy resin composition may be used as an adhesive film for a printed wiring board by applying the epoxy resin composition to a support film, followed by curing. An adhesive film may be prepared by a typical method known in the art, for example, a process wherein the epoxy resin composition is dissolved in an organic solvent, and the dissolved composition is coated onto a support film, followed by drying the organic solvent through heating or hot air blasting. As the organic solvent, ketones such as acetone or methylethylketone; acetic acid esters such as ethyl acetate or butyl acetate; carbitols such as cellosolve or butyl carbitol; aromatic hydrocarbons such as toluene; and amide solvents such as dimethylformamide may be used. These may be used alone or in combination thereof. Although drying conditions are not particularly limited, the organic solvent may be dried at about 50° C. to about 100° C. for about 1 to 10 minutes such that the organic solvent can be present in an amount of about 10 wt % or less in the coating layer. As the support film, polyolefins such as polyethylene or polypropylene, polyesters such as polyethylene terephthalate, polycarbonate, polyimide, and the like may be used. The support film may have a thickness of about 10 m to about 150 μm.

(3) Prepreg

The epoxy resin composition may be used as a prepreg by impregnating a sheet-like reinforcement substrate with the epoxy resin composition, followed by semi-curing through heating. The reinforcement substrate may include any suitable fibers generally used for prepregs, such as glass cloths or aramid fibers, without limitation.

A further aspect of the invention relates to an apparatus manufactured using the epoxy resin composition as set forth above. For example, the apparatus may include a semiconductor device encapsulated with the epoxy resin composition, a semiconductor apparatus or display including the same, and a multilayer wiring board including an adhesive film formed of the epoxy resin composition.

MODE FOR INVENTION

Hereinafter, the present invention will be described in more detail with reference to some examples. It should be understood that these examples are provided for illustration only and are not to be construed in any way as limiting the present invention.

Example 1

2.6 g of triphenylphosphine and 2.2 g of 4-nitrobenzyl bromide were dissolved in 30 ml of toluene, followed by reacting at 110° C. for 3 hours and then filtering and drying a produced precipitate, thereby obtaining 3.0 g of a solid. 3.0 g of the obtained solid was dissolved in 50 ml of methylene chloride, followed by reacting with 1.2 g of sodium sulfadiazine at 25° C. for 24 hours and then filtering a produced precipitate to obtain a liquid, which in turn was subjected to distillation under reduced pressure (evaporating), thereby obtaining 1.0 g of a solid. The solid was identified by NMR data as a compound represented by Formula 9:

[Formula 9]

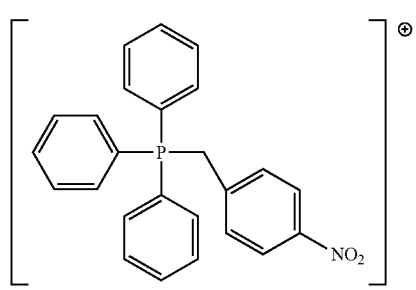

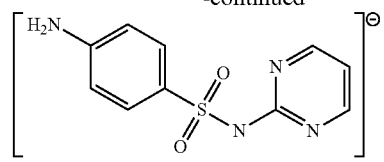

$^1$H NMR (400 MHz, DMSO) 8.30 (d, J=2.2 Hz, 2H), 8.10 (m, 2H), 7.93 (m, 3H), 7.82-7.65 (m, 14H), 7.27 (m, 2H), 6.75 (d, J=2.2 Hz, 2H), 6.50 (m, 1H), 5.45 (d, J=5.2 Hz, 2H), 1.62 (br s, 2H) ppm; $^{13}$C NMR (100 MHz, DMSO) 169.2, 157.8, 157.7, 151.9, 145.5, 135.1, 134.4, 131.2, 130.2, 130.1, 129.9, 129.8, 128.1, 128.0, 122.4, 122.8, 118.8, 118.1, 116.6, 116.5, 110.5 ppm; $^{31}$P NMR (166 MHz, DMSO) 24.29 ppm; LC-MS m/z=647 (M$^+$); Anal. Calcd for C$_{35}$H$_{30}$N$_5$O$_4$PS: C, 64.90; H, 4.67; N, 10.81; S, 4.95. Found: C, 64.97; H, 4.56; N, 10.99; S, 4.58.

Example 2

2.6 g of triphenylphosphine and 1.7 g of benzyl bromide were dissolved in 30 ml of toluene, followed by reacting at 110° C. for 3 hours and then filtering and drying a produced precipitate, thereby obtaining 3.0 g of a solid. 3.0 g of the obtained solid was dissolved in 50 ml of methylene chloride, followed by reacting with 1.2 g of sodium sulfadiazine at room temperature for 24 hours and then filtering a produced precipitate to obtain a liquid, which in turn was subjected to distillation under reduced pressure (evaporating), thereby obtaining 1.0 g of a solid. The solid was identified by NMR data as a compound represented by Formula 10:

[Formula 10]

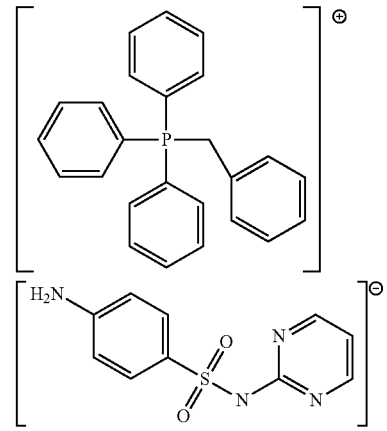

$^1$H NMR (400 MHz, DMSO) 8.31 (d, J=2.2 Hz, 2H), 7.90-6.94 (m, 22H), 6.74 (d, J=2.2 Hz, 2H), 6.58 (m, 1H), 5.48 (d, J=5.4 Hz, 2H), 2.1 (br s, 2H) ppm; $^{13}$C NMR (100 MHz, DMSO) 169.3, 157.9, 157.8, 151.6, 135.1, 134.5, 134.4, 131.2, 130.2, 130.1, 129.9, 129.8, 129.7, 128.3, 128.2, 128.1, 127.8, 118.8, 118.1, 116.6, 116.5, 110.3 ppm; $^{31}$P NMR (166 MHz, DMSO) 24.15 ppm; LC-MS m/z=602 (M$^+$); Anal. Calcd for C$_{35}$H$_{31}$N$_4$O$_2$PS: C, 69.75; H, 5.18; N, 9.30; S, 5.31. Found: C, 69.48; H, 5.37; N, 9.33; S, 5.52.

Example 3

3.0 g of tetraphenylphosphonium bromide was dissolved in 50 ml of methylene chloride, followed by reacting with 1.2 g of silver 4-amino-N-(5-methyl-2-pyrimidinyl)-benzenesulfonamide at room temperature for 24 hours and then filtering a produced precipitate to obtain a liquid, which in turn was subjected to distillation under reduced pressure (evaporating), thereby obtaining 1.0 g of a solid. The solid was identified by NMR data as a compound represented by Formula 11:

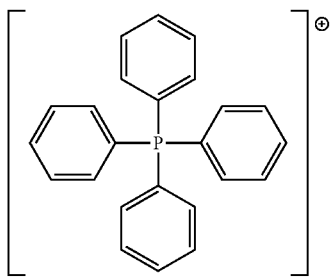

[Formula 11]

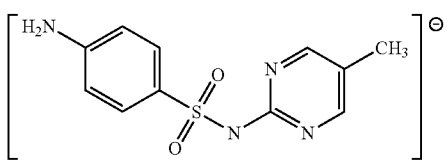

$^1$H NMR (400 MHz, DMSO) 8.17 (s, 2H), 8.05-7.65 (m, 22H), 6.74 (d, J=2.2 Hz, 2H), 2.0 (br s, 2H) ppm; $^{13}$C NMR (100 MHz, DMSO) 167.0, 157.7, 157.6, 151.6, 135.1, 134.2, 134.1, 130.3, 130.2, 130.0, 129.7, 128.1, 128.0, 118.8, 118.5, 118.0, 116.6, 116.5, 24.3 ppm; $^{31}$P NMR (166 MHz, DMSO) 24.30 ppm; LC-MS m/z=602 (M$^+$); Anal. Calcd for C$_{35}$H$_{31}$N$_4$O$_2$PS: C, 69.75; H, 5.18; N, 9.30; S, 5.31.

Found: C, 69.76; H, 5.44; N, 9.57; S, 5.64.

Example 4

3.0 g of tetraphenylphosphonium bromide was dissolved in 50 ml of methylene chloride, followed by reacting with 1.2 g of silver 4-(methylamino)-N-(pyrimidin-2-yl)benzenesulfonamide at room temperature for 24 hours and then filtering a produced precipitate to obtain a liquid, which in turn was subjected to distillation under reduced pressure (evaporating), thereby obtaining 1.0 g of a solid. The solid was identified by NMR data as a compound represented by Formula 12:

[Formula 12]

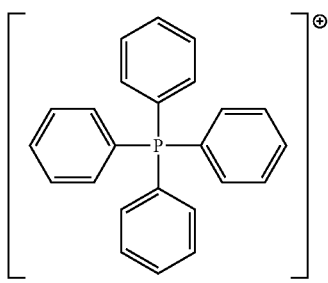

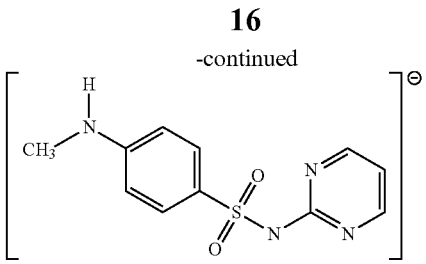

$^1$H NMR (400 MHz, DMSO) 8.38 (d, J=2.2 Hz, 2H), 8.05-7.65 (m, 22H), 6.71 (d, J=2.2 Hz, 2H), 6.58 (m, 1H), 3.40 (br s, 1H), 2.78 (s, 3H) ppm; $^{13}$C NMR (100 MHz, DMSO) 169.1, 157.9, 157.8, 150.8, 135.1, 134.2, 134.1, 130.3, 130.2, 128.2, 128.1, 128.0, 118.8, 118.5, 113.9, 113.8, 110.3, 29.7 ppm; $^{31}$P NMR (166 MHz, DMSO) 24.28 ppm; LC-MS m/z=602 (M$^+$); Anal. Calcd for C$_{35}$H$_{31}$N$_4$O$_2$PS: C, 69.75; H, 5.18; N, 9.30; S, 5.31. Found: C, 69.43; H, 5.15; N, 9.64; S, 5.38.

Example 5

3.0 g of tetraphenylphosphonium bromide and 2.5 g of sodium 4-methyl-N-propylbenzenesulfonamide were dissolved in 50 ml of a methylene chloride/H$_2$O 1:1 solution, followed by reacting at room temperature for 24 hours and then filtering a produced precipitate to obtain a liquid, which in turn was subjected to distillation under reduced pressure (evaporating), thereby obtaining 3.0 g of a solid. The solid was identified by NMR data as a compound represented by Formula 13:

[Formula 13]

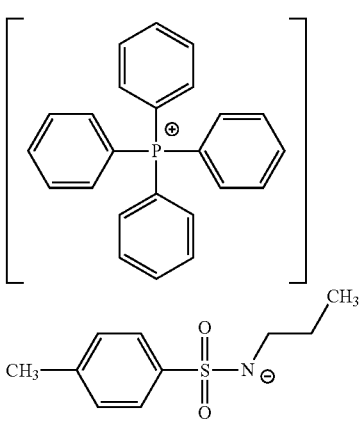

$^1$H NMR (400 MHz, DMSO) 7.96 (t, J=2.4 Hz, 4H), 7.85-7.80 (m, 8H), 7.75-7.70 (m, 8H), 7.69 (d, J=6.0 Hz, 2H), 7.27 (d, J=6.0 Hz, 2H), 3.16 (t, J=6.4 Hz, 2H), 2.35 (s, 3H), 1.59 (m, 2H), 0.96 (t, J=7.2 Hz, 2H) ppm; $^{13}$C NMR (100 MHz, DMSO) 141.6, 137.4, 137.3, 129.4, 128.9, 128.8, 127.2, 45.0, 24.3, 22.3, 11.2 ppm; $^{31}$P NMR (166 MHz, DMSO) 24.20 ppm; LC-MS m/z=551 (M$^+$); Anal. Calcd for C$_{34}$H$_{34}$NO$_2$PS: C, 74.02; H, 6.21; N, 2.54; S, 5.81. Found: C, 74.34; H, 6.19; N, 2.87; S, 5.69.

Example 6

3.0 g of tetraphenylphosphonium bromide and 3.0 g of sodium N-(4-aminophenylsulfonyl)benzamide were dissolved in 50 ml of a methylene chloride/H$_2$O 1:1 solution, followed by reacting at room temperature for 24 hours and then filtering a produced precipitate to obtain a liquid, which in turn was subjected to distillation under reduced pressure (evaporating), thereby obtaining 3.2 g of a solid. The solid was identified by NMR data as a compound represented by Formula 14:

[Formula 14]

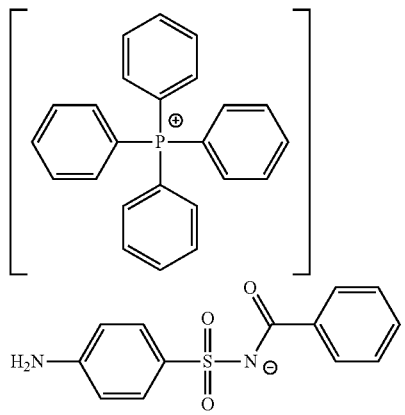

$^1$H NMR (400 MHz, DMSO) 7.97 (t, J=2.6 Hz, 4H), 7.88 (d, J=2.2 Hz, 2H), 7.84-7.81 (m, 8H), 7.76-7.72 (m, 8H), 7.52 (d, J=6.0 Hz, 2H), 7.31-7.25 (m, 3H), 6.47 (d, J=6.0 Hz, 2H), 5.23 (s, 2H) ppm; $^{13}$C NMR (100 MHz, DMSO) 170.1, 151.6, 137.3, 134.2, 132.2, 129.7, 128.9, 128.8, 128.1, 127.5, 116.6 ppm; $^{31}$P NMR (166 MHz, DMSO) 24.10 ppm; LC-MS m/z=614 (M$^+$); Anal. Calcd for C$_{37}$H$_{31}$N$_2$O$_3$PS: C, 72.30; H, 5.08; N, 4.56; S, 5.22. Found: C, 72.42; H, 5.14; N, 4.75; S, 5.38.

Example 7

3.0 g of tetraphenylphosphonium bromide and 2.7 g of sodium sulfacetamide were dissolved in 50 ml of a methylene chloride/H$_2$O 1:1 solution, followed by reacting at room temperature for 24 hours and then filtering a produced precipitate to obtain a liquid, which in turn was subjected to distillation under reduced pressure (evaporating), thereby obtaining 3.0 g of a solid. The solid was identified by NMR data as a compound represented by Formula 15:

[Formula 15]

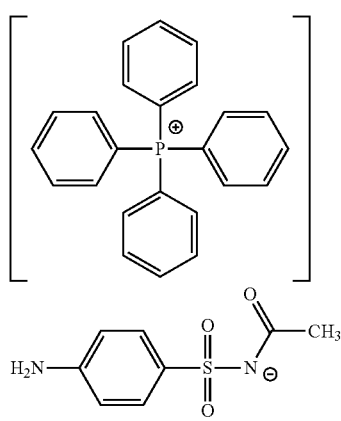

$^1$H NMR (400 MHz, DMSO) 7.97 (t, J=2.6 Hz, 4H), 7.84-7.81 (m, 8H), 7.76-7.72 (m, 8H), 7.42 (d, J=6.6 Hz, 2H), 6.47 (d, J=6.6 Hz, 2H), 5.23 (s, 2H), 1.66 (s, 3H) ppm; $^{13}$C NMR (100 MHz, DMSO) 173.2, 151.6, 137.4, 137.3, 129.7, 128.9, 128.8, 128.1, 116.6, 21.9 ppm; $^{31}$P NMR (166 MHz, DMSO) 24.30 ppm; LC-MS m/z=552 (M$^+$); Anal. Calcd for C$_{32}$H$_{29}$N$_2$O$_3$PS: C, 69.55; H, 5.29; N, 5.07; S, 5.80. Found: C, 69.48; H, 5.37; N, 5.11; S, 5.74.

Example 8

2.6 g of triphenylphosphine and 1.6 g of 4-bromophenol were dissolved in 5 ml of ethylene glycol, followed by reacting at 180° C. for 5 hours and then filtering and drying a produced precipitate, thereby obtaining 2.2 g of a solid. 3.0 g of the obtained solid and 2.7 g of sodium sulfacetamide were dissolved in 50 ml of a methylene chloride/H$_2$O 1:1 solution, followed by reacting at room temperature for 24 hours and then collecting an MC layer, thereby obtaining a liquid, which in turn was subjected to distillation under reduced pressure (evaporating), thereby obtaining 4.0 g of a solid. The solid was identified by NMR data as a compound represented by Formula 16:

[Formula 16]

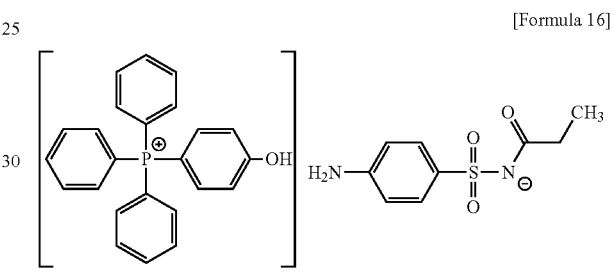

$^1$H NMR (400 MHz, DMSO) 7.97-7.90 (m, 3H), 7.78-7.65 (m, 12H), 7.42 (d, J=6.6 Hz, 2H), 7.38 (d, J=8.6 Hz, 2H), 6.97 (d, J=8.6 Hz, 2H), 6.47 (d, J=6.6 Hz, 2H), 5.54 (s, 1H), 4.12 (br, 2H), 1.66 (s, 3H) ppm; $^{13}$C NMR (100 MHz, DMSO) 173.1, 158.6, 151.6, 138.7, 137.4, 137.3, 129.7, 128.9, 128.8, 128.1, 116.6, 115.9, 21.9 ppm; $^{31}$P NMR (166 MHz, DMSO) 24.20 ppm; LC-MS m/z=568 (M$^+$); Anal. Calcd for C$_{32}$H$_{29}$N$_2$O$_4$PS: C, 67.59; H, 5.14; N, 4.93; S, 5.64. Found: C, 67.47; H, 5.29; N, 4.84; S, 5.49.

Example 9

7.5 parts by weight of a biphenyl type epoxy resin (NC-3000, Nippon Kayaku), 4.7 parts by weight of a xyloc type phenol resin (HE100C-10, Air Water), 0.2 parts by weight of the compound in Example 1, 86 parts by weight of inorganic fillers obtained by mixing spherical fused silica having an average particle diameter of 18 m with spherical fused silica having an average particle diameter of 0.5 m in a weight ratio of 9:1, 0.6 parts by weight of a coupling agent obtained by mixing 0.3 parts by weight of mercaptopropyltrimethoxysilane (KBM-803, Shin-Etsu Co., Ltd.) with 0.3 parts by weight of methyltrimethoxysilane (SZ-6070, Dow Corning Chemical Co., Ltd.), 0.5 parts by weight of Carnauba wax as a release agent, and 0.5 parts by weight of carbon black (MA-600, Matsushita Chemical Co., Ltd.) as a coloring agent were mixed, followed by uniformly stirring using a Henschel mixer, thereby obtaining a powdery composition. Then, the obtained powder was subjected to melt kneading using a continuous kneader at 95° C., followed by cooling and pulverizing, thereby preparing an epoxy resin composition.

Example 10

An epoxy resin composition was prepared in the same manner as in Example 9 except that the compound in Example 2 was used instead of the compound in Example 1.

Example 11

An epoxy resin composition was prepared in the same manner as in Example 9 except that the compound in Example 3 was used instead of the compound in Example 1.

Example 12

An epoxy resin composition was prepared in the same manner as in Example 9 except that the compound in Example 4 was used instead of the compound in Example 1.

Example 13

An epoxy resin composition was prepared in the same manner as in Example 9 except that 7.5 parts by weight of a biphenyl type epoxy resin, 4.8 parts by weight of a xyloc type phenol resin, 0.1 parts by weight of the compound prepared in Example 1, 86 parts by weight of inorganic fillers, 0.6 parts by weight of a coupling agent, 0.5 parts by weight of a release agent, and 0.5 parts by weight of a coloring agent were mixed.

Example 14

An epoxy resin composition was prepared in the same manner as in Example 9 except that a phenol aralkyl type epoxy resin was used instead of the biphenyl type epoxy resin.

Example 15

An epoxy resin composition was prepared in the same manner as in Example 9 except that a cresol novolac type epoxy resin was used instead of the biphenyl type epoxy resin.

Example 16

An epoxy resin composition was prepared in the same manner as in Example 9 except that a phenol novolac type phenol resin was used instead of the xyloc type phenol resin.

Example 17

An epoxy resin composition was prepared in the same manner as in Example 9 except that a phenol aralkyl type phenol resin was used instead of the xyloc type phenol resin.

Example 18

An epoxy resin composition was prepared in the same manner as in Example 9 except that a mixture of 0.1 parts by weight of the compound prepared in Example 1 and 0.1 parts by weight of triphenylphosphine was used instead of 0.2 parts by weight of the compound in Example 1.

Example 19

An epoxy resin composition was prepared in the same manner as in Example 9 except that the compound in Example 5 was used instead of the compound in Example 1.

Example 20

An epoxy resin composition was prepared in the same manner as in Example 9 except that the compound in Example 6 was used instead of the compound in Example 1.

Example 21

An epoxy resin composition was prepared in the same manner as in Example 9 except that the compound in Example 7 was used instead of the compound in Example 1.

Example 22

An epoxy resin composition was prepared in the same manner as in Example 9 except that the compound in Example 8 was used instead of the compound in Example 1.

Comparative Example 1

An epoxy resin composition was prepared in the same manner as in Example 9 except that the compound of Example 1 was not used.

Comparative Example 2

An epoxy resin composition was prepared in the same manner as in Example 9 except that triphenylphosphine was used instead of the compound in Example 1.

Comparative Example 3

An epoxy resin composition was prepared in the same manner as in Example 9 except that an triphenylphosphine-1,4-benzoquinone adduct was used instead of the compound prepared in Example 1.

The epoxy resin compositions prepared in Examples and Comparative Examples were evaluated as to their physical properties by way of the following measuring methods. Results are summarized in Tables 1 and 2.

TABLE 1

| | | Example | | | | | | | | |
|---|---|---|---|---|---|---|---|---|---|---|
| | | 9 | 10 | 11 | 12 | 13 | 14 | 15 | 16 | 17 |
| Basic physical properties | Flowability (inch) | 73 | 71 | 74 | 73 | 67 | 65 | 71 | 69 | 68 |
| | Curing shrinkage (%) | 0.35 | 0.34 | 0.37 | 0.38 | 0.33 | 0.35 | 0.34 | 0.33 | 0.33 |
| | Glass transition temp. (° C.) | 122 | 123 | 124 | 124 | 121 | 123 | 121 | 123 | 121 |
| | Moisture absorption rate (%) | 0.24 | 0.25 | 0.24 | 0.24 | 0.25 | 0.25 | 0.24 | 0.24 | 0.25 |

TABLE 1-continued

|  |  | Example |  |  |  |  |  |  |  |  |
|---|---|---|---|---|---|---|---|---|---|---|
|  |  | 9 | 10 | 11 | 12 | 13 | 14 | 15 | 16 | 17 |
|  | Adhesive strength (kgf) | 77 | 74 | 75 | 74 | 76 | 74 | 75 | 77 | 76 |
|  | Rate of viscosity change (%) | 8.1 | 7.8 | 7.7 | 7.9 | 8.2 | 7.8 | 7.9 | 7.6 | 7.7 |
| Evaluation of packages | Degree of cure (Shore D) according to curing time — 50 sec | 71 | 69 | 72 | 70 | 68 | 69 | 70 | 69 | 71 |
|  | 60 sec | 73 | 71 | 74 | 72 | 70 | 71 | 72 | 72 | 74 |
|  | 70 sec | 75 | 73 | 76 | 75 | 73 | 75 | 75 | 74 | 75 |
|  | 80 sec | 78 | 76 | 76 | 76 | 74 | 75 | 76 | 74 | 76 |
|  | 90 sec | 78 | 76 | 78 | 77 | 74 | 75 | 76 | 74 | 76 |
| Storage stability | 24 hr | 98% | 97% | 97% | 96% | 98% | 97% | 98% | 98% | 98% |
|  | 48 hr | 94% | 95% | 94% | 92% | 96% | 94% | 96% | 96% | 95% |
|  | 72 hr | 91% | 93% | 90% | 89% | 92% | 91% | 92% | 93% | 92% |
| Reliability | Number of packages suffering cracking | 0 | 0 | 0 | 0 | 0 | 0 | 0 | 0 | 0 |
|  | Number of packages suffering peeling | 0 | 0 | 0 | 0 | 0 | 0 | 0 | 0 | 0 |
|  | Number of tested semiconductors | 88 | 88 | 88 | 88 | 88 | 88 | 88 | 88 | 88 |

TABLE 2

|  |  | Example |  |  |  |  | Comparative Example |  |  |
|---|---|---|---|---|---|---|---|---|---|
|  |  | 18 | 19 | 20 | 21 | 22 | 1 | 2 | 3 |
| Basic physical properties | Flowability (inch) | 59 | 70 | 71 | 72 | 74 | x* | 52 | 58 |
|  | Curing shrinkage (%) | 0.39 | 0.35 | 0.33 | 0.34 | 0.33 | x | 0.42 | 0.40 |
|  | Glass transition temp. (° C.) | 122 | 124 | 124 | 123 | 123 | x | 121 | 122 |
|  | Moisture absorption rate (%) | 0.25 | 0.24 | 0.25 | 0.24 | 0.24 | x | 0.25 | 0.26 |
|  | Adhesive strength (kgf) | 74 | 73 | 74 | 75 | 75 | x | 72 | 74 |
|  | Rate of viscosity change (%) | 15.2 | 8.3 | 8.0 | 7.7 | 7.5 | x | 27.3 | 30.2 |
| Evaluation of packages | Degree of cure (Shore D) according to curing time — 50 sec | 62 | 69 | 70 | 71 | 69 | x | 52 | 60 |
|  | 60 sec | 63 | 71 | 72 | 73 | 71 | x | 60 | 64 |
|  | 70 sec | 66 | 72 | 73 | 74 | 72 | x | 64 | 66 |
|  | 80 sec | 69 | 73 | 75 | 74 | 73 | x | 67 | 70 |
|  | 90 sec | 71 | 73 | 75 | 74 | 73 | x | 69 | 71 |
| Storage stability | 24 hr | 91% | 97% | 97% | 97% | 97% | x | 90% | 92% |
|  | 48 hr | 87% | 95% | 94% | 95% | 95% | x | 84% | 88% |
|  | 72 hr | 81% | 91% | 93% | 94% | 91% | x | 74% | 79% |
| Reliability | Number of packages suffering cracking | 0 | 0 | 0 | 0 | 0 | x | 0 | 0 |

TABLE 2-continued

|  | Example | | | | | Comparative Example | | |
|---|---|---|---|---|---|---|---|---|
|  | 18 | 19 | 20 | 21 | 22 | 1 | 2 | 3 |
| Number of packages suffering peeling | 0 | 0 | 0 | 0 | 0 | x | 45 | 20 |
| Number of tested semiconductors | 88 | 88 | 88 | 88 | 88 | 88 | 88 | 88 |

Note:
x means that the epoxy resin composition was not cured and thus data measurement on the epoxy resin composition was not possible.

(1) Flowability (inches): The flow length of each of the epoxy resin compositions was measured using a transfer molding press in a testing mold at 175° C. and 70 kgf/cm² in accordance with EMMI-1-66. A higher measured value indicates better flowability.

(2) Curing shrinkage (%): Each of the epoxy resin compositions was molded using a transfer molding press in an ASTM mold for flexural strength specimen construction at 175° C. and 70 kgf/cm² to obtain a molded specimen (125 mm×12.6 mm×6.4 mm). The specimen was subjected to post-molding curing (PMC) in an oven at 170° C. to 180° C. for 4 hours. After cooling, the length of the specimen was measured using calipers. Curing shrinkage of the epoxy resin composition was calculated by Equation 2:

$$\text{Curing shrinkage} = |C-D|/C \times 100 \quad \text{[Equation 2]}$$

(where C is the length of a specimen obtained by transfer molding of the epoxy resin composition at 175° C. under a load of 70 kgf/cm², and D is the length of the specimen after post-curing the specimen at 170° C. to 180° C. for 4 hours and cooling.)

(3) Glass transition temperature (° C.): Glass transition temperature was measured using a thermomechanical analyzer (TMA). TMA was set to measure glass transition temperature by heating at a rate of 10° C./min from 25° C. to 300° C.

(4) Moisture absorption rate (%): Each of the resin compositions prepared in Examples and Comparative Examples was molded at a mold temperature of 170° C. to 180° C., a clamp pressure of 70 kg/cm², a transfer pressure of 1,000 psi and a transfer speed of 0.5 to 1 cm/s for a curing time of 120 sec to obtain a cured specimen in the form of a disc having a diameter of 50 mm and a thickness of 1.0 mm. The specimen was subjected to post-molding curing (PMC) in an oven at 170° C. to 180° C. for 4 hours and left at 85° C. and 85% RH for 168 hours, followed by measuring a weight change of the specimen due to moisture absorption, thereby calculating a moisture absorption rate according to Equation 3:

$$\text{Moisture absorption rate (\%)} = (\text{Weight of specimen after moisture absorption} - \text{Weight of specimen before moisture absorption}) \div (\text{Weight of specimen before moisture absorption}) \times 100 \quad \text{[Equation 3]}$$

(5) Adhesive strength (kgf): A copper metal device having a size adapted to a mold for adhesive strength measurement was prepared as a test piece. Each of the resin compositions prepared in Examples and Comparative Examples was molded on the test piece at a mold temperature of 170° C. to 180° C., a clamp pressure of 70 kgf/cm², a transfer pressure of 1,000 psi and a transfer speed of 0.5 to 1 cm/s for a curing time of 120 sec to obtain a cured specimen. The specimen was subjected to post-molding curing (PMC) in an oven at 170° C. to 180° C. for 4 hours. The area of the epoxy resin composition in contact with the specimen was 40±1 mm², and the adhesive strength of the epoxy resin composition was measured with respect to 12 specimens in each measurement process using a universal testing machine (UTM) and the measured adhesive strength values were averaged.

(6) Rate of viscosity change: Viscosity of each of the epoxy resin compositions was measured at 25° C., and viscosity of each of the epoxy resin compositions was measured at 25° C. after leaving the specimen at 25° C. for 24 hours, followed by calculating rate of viscosity change according to Equation 1. Viscosity was measured using a coaxial double cylinder type rotary viscometer (PM-2 A, Malcomtech International). A lower rate of viscosity change indicates that the epoxy resin composition was less cured and thus exhibited high storage stability:

$$\text{Rate of change in viscosity} = |B-A|/A \times 100 \quad \text{[Equation 1]}$$

(where A is the viscosity (unit: cPs) of the epoxy resin composition as measured at 25° C., and B is the viscosity (unit: cPs) of the epoxy resin composition as measured at 25° C. after leaving the epoxy resin composition at 25° C. for 24 hours).

(7) Degree of cure (Shore-D): Each of the epoxy resin compositions was cured using a multi plunger system (MPS) equipped with a mold at 175° C. for 50 sec, 60 sec, 70 sec, 80 sec, and 90 sec to construct exposed thin quad flat packages (eTQFPs), each including a copper metal device having a width of 24 mm, a length of 24 mm and a thickness of 1 mm. Hardness of the cured products in the packages on the mold according to the curing periods of time were directly measured using a Shore D durometer. A higher hardness value indicates better degree of cure.

(8) Storage stability (%): The flow length of each of the epoxy resin compositions was measured in accordance with the method described in (1) while storing the compositions for one week in a thermo-hygrostat set to at 25° C./50% RH at an interval of 24 hours. Percent (%) of the flow length after storage to the flow length immediately after preparation of the composition was calculated. A higher value indicates better storage stability.

(9) Reliability: Each of eTQFP packages for evaluation of flexural properties was dried at 125° C. for 24 hours, followed by 5 cycles of thermal shock testing (1 cycle refers to a series of leaving the package alone at −65° C. for 10 min, at 25° C. for 10 min, and at 150° C. for 10 min). Then, the package was left at 85° C. and 60% RH for 168 hours and treated by IR reflow three times at 260° C. for 30 sec (preconditioning), followed by observing occurrence of external cracks on the package using an optical microscope. Next, the occurrence of peeling between the epoxy resin composition and a lead frame was evaluated using C-mode scanning acoustic microscopy (C-SAM) which is a non-destructive test method. External cracks of the package or peeling between the epoxy resin composition and the lead frame mean that reliability of the package cannot be guaranteed.

As shown in Table 1, it could be seen that the epoxy resin compositions including the phosphonium ion-containing compound according to the present invention had high flowability, low curing shrinkage, and high degrees of curing even in shorter curing periods of time in view of curability for each curing period of time. In addition, the epoxy resin compositions according to the present invention showed less change in flowability and had low rate of viscosity change after 72 hours, thereby exhibiting high storage stability. Further, it could be seen that the epoxy resin compositions according to the present invention did not suffer from cracking, and thus had excellent crack resistance while preventing peeling.

On the contrary, the compositions prepared in Comparative Examples and not including the phosphonium ion-containing compound of the present invention or including the phosphonium ion-free curing catalyst instead of the phosphonium ion-containing compound had low storage stability, high curing shrinkage, and low flowability. Therefore, it could be seen that the composition of Comparative Examples in a package could not ensure the effects of the present invention.

The invention claimed is:

1. A phosphonium ion-containing compound represented by Formula 1:

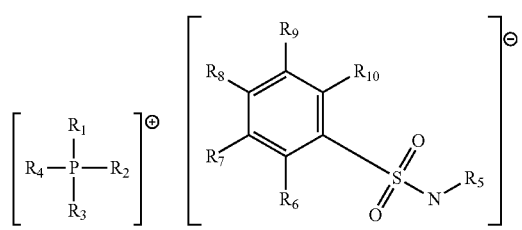

[Formula 1]

wherein, in Formula 1, $R_1$, $R_2$, $R_3$, and $R_4$ are each independently hydrogen, a substituted or unsubstituted $C_1$ to $C_{10}$ alkyl group, a substituted or unsubstituted $C_3$ to $C_{10}$ cycloalkyl group, a substituted or unsubstituted $C_6$ to $C_{20}$ aryl group, or a substituted or unsubstituted $C_7$ to $C_{21}$ arylalkyl group, provided that at least one of $R_1$, $R_2$, $R_3$, or $R_4$ is an unsubstituted $C_6$ to $C_{20}$ aryl group;

$R_5$ is hydrogen, a substituted or unsubstituted $C_1$ to $C_{10}$ alkyl group, a substituted or unsubstituted $C_6$ to $C_{20}$ aryl group, a substituted or unsubstituted $C_3$ to $C_{20}$ cycloalkyl group, a substituted or unsubstituted $C_2$ to $C_{20}$ heterocycloalkyl group, a substituted or unsubstituted $C_7$ to $C_{20}$ arylalkyl group, a substituted or unsubstituted $C_3$ to $C_{20}$ heteroaryl group, or a group represented by Formula 2:

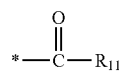

[Formula 2]

wherein, in Formula 2, * is a binding site to N in Formula 1, and $R_{11}$ is a substituted or unsubstituted $C_1$ to $C_{10}$ alkyl group, a substituted or unsubstituted $C_6$ to $C_{20}$ aryl group, a substituted or unsubstituted $C_3$ to $C_{10}$ cycloalkyl group, or a substituted or unsubstituted $C_7$ to $C_{20}$ arylalkyl group; and $R_6$, $R_7$, $R_8$, $R_9$, and $R_{10}$ are each independently hydrogen, a substituted or unsubstituted $C_1$ to $C_{10}$ alkyl group, a substituted or unsubstituted $C_6$ to $C_{20}$ aryl group, a substituted or unsubstituted $C_7$ to $C_{21}$ arylalkyl group, or —NR'R" in which R' and R" are each independently hydrogen, a $C_1$ to $C_{10}$ alkyl group, a $C_6$ to $C_{20}$ aryl group, or a $C_7$ to $C_{21}$ arylalkyl group.

2. The phosphonium ion-containing compound according to claim 1, wherein the phosphonium ion-containing compound decomposes as in Reaction Formula 1 at about 90° C. to about 175° C.:

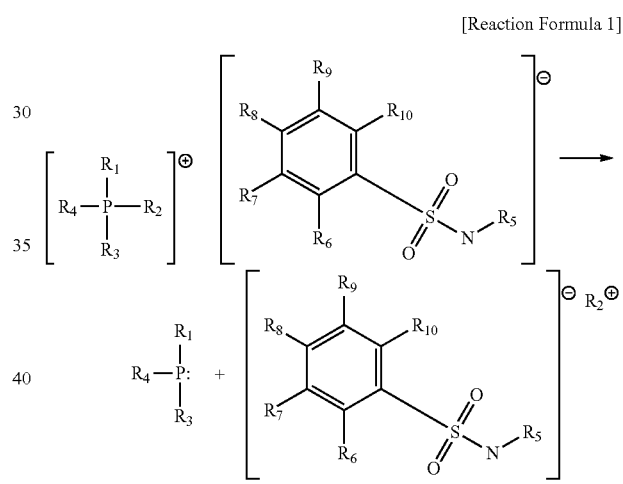

[Reaction Formula 1]

wherein, in Reaction Formula 1, $R_1$, $R_2$, $R_3$, $R_4$, $R_5$, $R_6$, $R_7$, $R_8$, $R_9$, and $R_{10}$ are the same as defined in Formula 1.

3. The phosphonium ion-containing compound according to claim 1, wherein $R_5$ is a substituted or unsubstituted $C_1$ to $C_4$ alkyl group, a substituted or unsubstituted $C_3$ to $C_{20}$ heteroaryl group, or a compound represented by Formula 2 in which $R_{11}$ is a substituted or unsubstituted $C_1$ to $C_5$ alkyl group or a substituted or unsubstituted $C_6$ to $C_{10}$ aryl group.

4. The phosphonium ion-containing compound according to claim 1, wherein:

$R_1$, $R_2$, $R_3$, and $R_4$ each independently include a substituted or unsubstituted $C_6$ to $C_{20}$ aryl group, at least one of $R_1$, $R_2$, $R_3$, or $R_4$ being an unsubstituted $C_6$ to $C_{20}$ aryl group, and $R_6$ is —NR'R" in which R' and R" are each independently hydrogen, a $C_1$ to $C_{10}$ alkyl group, a $C_6$ to $C_{20}$ aryl group, or a $C_7$ to $C_{21}$ arylalkyl group.

5. An epoxy resin composition, comprising:

an epoxy resin, a curing agent, and a curing catalyst, the curing catalyst including the phosphonium ion-containing compound according to claim 1.

6. The epoxy resin composition according to claim 5, wherein the epoxy resin includes an epoxy resin having two or more epoxy groups and one or more hydroxyl groups per molecule.

7. The epoxy resin composition according to claim 5, wherein the epoxy resin includes one or more of a bisphenol epoxy resin, a phenol novolac epoxy resin, a tert-butyl catechol epoxy resin, a naphthalene epoxy resin, a glycidyl amine epoxy resin, a phenol aralkyl epoxy resin, a cresol novolac epoxy resin, a biphenyl epoxy resin, a linear aliphatic epoxy resin, an alicyclic epoxy resin, a heterocyclic epoxy resin, a spiro ring-containing epoxy resin, a cyclohexane dimethanol epoxy resin, or a halogenated epoxy resin.

8. The epoxy resin composition according to claim 5, wherein the curing agent includes a phenol resin.

9. The epoxy resin composition according to claim 5, wherein the curing agent includes one or more of a phenolaralkyl phenol resin, a phenol novolac phenol resin, a xyloc phenol resin, a cresol novolac phenol resin, a naphthol phenol resin, a terpene phenol resin, a multifunctional phenol resin, a dicyclopentadiene-based phenol resin, a novolac phenol resin prepared from bisphenol A and resol, tris(hydroxyphenyl)methane, dihydroxybiphenyl, an acid anhydride, meta-phenylenediamine, diaminodiphenylmethane, or diaminodiphenylsulfone.

10. The epoxy resin composition according to claim 5, wherein the phosphonium ion-containing compound is present in an amount of about 0.01 wt % to about 5 wt % in the epoxy resin composition.

11. The epoxy resin composition according to claim 5, wherein the phosphonium ion-containing compound is present in an amount of about 10 wt % to 100 wt % in the curing catalyst.

12. The epoxy resin composition according to claim 5, further comprising an inorganic filler.

13. The epoxy resin composition according to claim 5, wherein the epoxy resin composition has a curing initiation temperature of about 90° C. to about 120° C.

14. The epoxy resin composition according to claim 5, wherein the epoxy resin composition has a rate of viscosity change of about 16% or less, as calculated according to Equation 1:

Rate of viscosity change=|B−A|/A×100    [Equation 1]

wherein, in Equation 1, A is the viscosity (unit: cPs) of the epoxy resin composition as measured at 25° C., and B is the viscosity (unit: cPs) of the epoxy resin composition as measured at 25° C. after leaving the epoxy resin composition at 25° C. for 24 hours.

15. The epoxy resin composition according to claim 5, wherein the epoxy resin composition has a flow length of about 59 to about 75 inches as measured using a transfer molding press at 175° C. under a load of 70 kgf/cm² in accordance with EMMI-1-66.

16. The epoxy resin composition according to claim 5, wherein the epoxy resin composition has a curing shrinkage of less than about 0.4% as calculated according to Equation 2:

Curing shrinkage=|C−D|/C×100    [Equation 2]

wherein, in Equation 2, C is the length of a specimen obtained by transfer molding of the epoxy resin composition at 175° C. under a load of 70 kgf/cm², and D is the length of the specimen after post-curing the specimen at 170° C. to 180° C. for 4 hours and cooling.

17. An epoxy resin composition for encapsulating a semiconductor device comprising the epoxy resin composition according to claim 5.

18. An apparatus manufactured using the epoxy resin composition according to claim 5.

19. A curing catalyst represented by Formula 1:

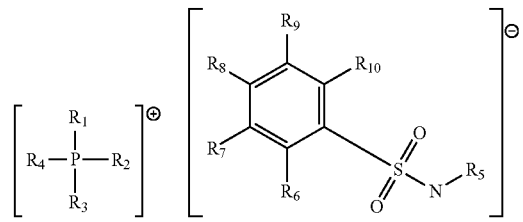

[Formula 1]

wherein, in Formula 1, $R_1$, $R_2$, $R_3$, and $R_4$ are each independently hydrogen, a substituted or unsubstituted $C_1$ to $C_{10}$ alkyl group, a substituted or unsubstituted $C_3$ to $C_{10}$ cycloalkyl group, a substituted or unsubstituted $C_6$ to $C_{20}$ aryl group, or a substituted or unsubstituted $C_7$ to $C_{21}$ arylalkyl group, provided that at least one of $R_1$, $R_7$, $R_3$, or $R_4$ is an unsubstituted $C_6$ to $C_{20}$ aryl group;

$R_5$ is hydrogen, a substituted or unsubstituted $C_1$ to $C_{10}$ alkyl group, a substituted or unsubstituted $C_6$ to $C_{20}$ aryl group, a substituted or unsubstituted $C_3$ to $C_{20}$ cycloalkyl group, a substituted or unsubstituted $C_2$ to $C_{20}$ heterocycloalkyl group, a substituted or unsubstituted $C_7$ to $C_{20}$ arylalkyl group, a substituted or unsubstituted $C_3$ to $C_{20}$ heteroaryl group, or a group represented by Formula 2:

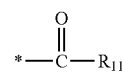

[Formula 2]

wherein, in Formula 2, * is a binding site to N in Formula 1, and $R_{11}$ is a substituted or unsubstituted $C_1$ to $C_{10}$ alkyl group, a substituted or unsubstituted $C_6$ to $C_{20}$ aryl group, a substituted or unsubstituted $C_3$ to $C_{19}$ cycloalkyl group, or a substituted or unsubstituted $C_7$ to $C_{20}$ arylalkyl group; and $R_6$, $R_7$, $R_8$, $R_9$, and $R_{10}$ are each independently hydrogen, a substituted or unsubstituted $C_1$ to $C_{10}$ alkyl group, a substituted or unsubstituted $C_6$ to $C_{20}$ aryl group, a substituted or unsubstituted $C_7$ to $C_{21}$ arylalkyl group, or —NR'R" in which R' and R" are each independently hydrogen, a $C_1$ to $C_{10}$ alkyl group, a $C_6$ to $C_{20}$ aryl group, or a $C_7$ to $C_{21}$ arylalkyl group.

* * * * *